(12) United States Patent  (10) Patent No.: US 8,776,797 B2
Brain  (45) Date of Patent: *Jul. 15, 2014

(54) LARYNGEAL MASK AIRWAY DEVICE

(75) Inventor: Archibald I. J. Brain, Victoria (SC)

(73) Assignee: The Laryngeal Mask Company Ltd., Victoria Mahe (SC)

( * ) Notice: Subject to any disclaimer, the term of this patent is extended or adjusted under 35 U.S.C. 154(b) by 0 days.

This patent is subject to a terminal disclaimer.

(21) Appl. No.: 13/267,421

(22) Filed: Oct. 6, 2011

(65) Prior Publication Data

US 2012/0085351 A1    Apr. 12, 2012

Related U.S. Application Data

(63) Continuation of application No. 11/915,556, filed as application No. PCT/GB2006/001913 on May 24, 2006, now abandoned.

(30) Foreign Application Priority Data

May 27, 2005    (GB) .................................... 0510951.7

(51) Int. Cl.
*A61M 16/04*    (2006.01)
(52) U.S. Cl.
CPC .................................... *A61M 16/04* (2013.01)
USPC ............. 128/207.15; 128/207.14; 128/200.26
(58) Field of Classification Search
CPC ..................... A61M 2016/0409; A61M 16/04; A61M 2016/0415; A61M 16/0463; A61M 16/0488; A61M 16/0434; A61M 2016/0493; A61M 16/0057; A61M 2016/0486; A61M 2210/0656; A61M 2016/0445; A61M 2016/0616; A61M 2016/0825; A61M 2202/0468; A61M 2202/0488; A61M 2210/065; A61M 25/01
USPC .............. 128/200.24, 200.26, 207.14, 207.15
See application file for complete search history.

(56) References Cited

U.S. PATENT DOCUMENTS

| 4,509,514 | A | | 4/1985 | Brain |
| 4,995,388 | A | | 2/1991 | Brain et al. |
| 5,113,875 | A | * | 5/1992 | Bennett .............................. 5/648 |
| 5,241,956 | A | * | 9/1993 | Brain ....................... 128/207.15 |
| 5,249,571 | A | | 10/1993 | Brain et al. |
| 5,282,464 | A | | 2/1994 | Brain et al. |
| 5,297,547 | A | | 3/1994 | Brain et al. |
| 5,303,697 | A | | 4/1994 | Brain et al. |
| 5,355,879 | A | | 10/1994 | Brain et al. |
| 5,623,921 | A | * | 4/1997 | Kinsinger et al. ....... 128/200.26 |

(Continued)

FOREIGN PATENT DOCUMENTS

GB        2205499        12/1988

*Primary Examiner* — Annette Dixon
(74) *Attorney, Agent, or Firm* — Wilmer Cutler Pickering Hale and Dorr LLP

(57) ABSTRACT

A laryngeal mask airway device for insertion into a patient to provide an airway passage to the patient's glottic opening. The device includes an airway tube, a mask attached to the airway tube, a peripheral inflatable cuff, and an outlet for gas. The mask is attached to the airway tube for gaseous communication between the tube and an outlet. The device further includes an oesophageal drain that includes a conduit that extends from an inlet at the distal end of the mask to an outlet disposed outside the patient when the device is in place. The conduit includes a mask section and airway tube section, wherein the mask section is formed integrally in the material of the body of the mask.

15 Claims, 16 Drawing Sheets

(56) References Cited

U.S. PATENT DOCUMENTS

| | | | |
|---|---|---|---|
| 5,632,271 A * | 5/1997 | Brain | 128/207.15 |
| RE35,531 E * | 6/1997 | Callaghan et al. | 128/207.15 |
| 5,791,341 A * | 8/1998 | Bullard | 128/207.15 |
| 5,878,745 A * | 3/1999 | Brain | 128/207.15 |
| 5,976,072 A * | 11/1999 | Greenberg | 600/120 |
| 6,079,409 A | 6/2000 | Brain et al. | |
| 6,119,695 A * | 9/2000 | Augustine et al. | 128/207.15 |
| 6,439,232 B1 * | 8/2002 | Brain | 128/207.15 |
| 6,631,720 B1 * | 10/2003 | Brain | 128/207.14 |
| 7,004,169 B2 * | 2/2006 | Brain | 128/207.14 |
| RE39,938 E * | 12/2007 | Brain | 128/207.15 |
| 2004/0020491 A1 * | 2/2004 | Fortuna | 128/207.15 |
| 2008/0308109 A1 * | 12/2008 | Brain | 128/207.14 |
| 2009/0133701 A1 * | 5/2009 | Brain | 128/207.14 |
| 2010/0059061 A1 * | 3/2010 | Brain | 128/207.14 |
| 2012/0145161 A1 * | 6/2012 | Brain | 128/207.15 |

\* cited by examiner

LARYNGEAL MASK AIRWAY DEVICE

CROSS-REFERENCE TO RELATED APPLICATIONS

This application is a continuation of co-pending U.S. patent application Ser. No. 11/915,556, filed Dec. 5, 2008, entitled "Laryngeal Mask Airway Device", which is a 371 National Phase application of International Application PCT/GB06/01913, filed May 24, 2006, entitled "Laryngeal Mask Airway Device", which claims priority to United Kingdom application GB 0510951.7, filed May 27, 2005, entitled "Laryngeal Mask Airway Device", each of which is incorporated by reference herein in its entirety.

BACKGROUND OF THE INVENTION

1. Field of the Invention

The present invention relates to a laryngeal mask airway device.

2. Description of Related Art Including Information Disclosed Under 37 C.F.R. 1.97 and 1.98

The laryngeal mask airway device is a well known device that is useful for establishing airways in unconscious patients. U.S. Pat. No. 4,509,514 is one of the many publications that describe laryngeal mask airway devices. Such devices have been in use for many years and offer an alternative to the older, even better known endotracheal tube. For at least seventy years, endotracheal tubes comprising a long slender tube with an inflatable balloon disposed at the tube's distal end have been used for establishing airways in unconscious patients. In operation, the endotracheal tube's distal end is inserted through the mouth of the patient, past the patient's trachea. Once so positioned, the balloon is inflated so as to form a seal with the interior lining of the trachea. After this seal is established, positive pressure may be applied to the tube's proximal end to ventilate the patient's lungs. Also, the seal between the balloon and the inner lining of the trachea protects the lungs from aspiration (e.g., the seal prevents material regurgitated from the stomach from being aspirated into the patient's lungs).

Although they have been enormously successful, endotracheal tubes suffer from several major disadvantages. The principal disadvantage of the endotracheal tube relates to the difficulty of properly inserting the tube. Inserting an endotracheal tube into a patient is a procedure that requires a high degree of skill. Also, even for skilled practitioners, insertion of an endotracheal tube is sometimes difficult or not possible. In many instances, the difficulty of inserting endotracheal tubes has tragically led to the death of a patient because it was not possible to establish an airway in the patient with sufficient rapidity. Also, inserting an endotracheal tube normally requires manipulation of the patient's head and neck and further requires the patient's jaw to be forcibly opened widely. These necessary manipulations make it difficult, or undesirable, to insert an endotracheal tube into a patient who may be suffering from a neck injury.

In contrast to the endotracheal tube, it is relatively easy to insert a laryngeal mask airway device into a patient and thereby establish an airway. Also, the laryngeal mask airway device is a "forgiving" device in that even if it is inserted improperly, it still tends to establish an airway. Accordingly, the laryngeal mask airway device is often thought of as a "life saving" device. Also, the laryngeal mask airway device may be inserted with only relatively minor manipulation of the patient's head, neck and jaw. Further, the laryngeal mask airway device provides ventilation of the patient's lungs without requiring contact with the sensitive inner lining of the trachea and the size of the airway established is typically significantly larger than the size of the airway established with an endotracheal tube. Also, the laryngeal mask airway device does not interfere with coughing to the same extent as endotracheal tubes. Largely due to these advantages, the laryngeal mask airway device has enjoyed increasing popularity in recent years.

U.S. Pat. Nos. 5,303,697 and 6,079,409 describe examples of prior art devices that may be referred to as "intubating laryngeal mask airway devices." The intubating device has the added advantage that it is useful for facilitating insertion of an endotracheal tube. After an intubating laryngeal mask airway device has been located in the patient, the device can act as a guide for a subsequently inserted endotracheal tube. Use of the laryngeal mask airway device in this fashion facilitates what is commonly known as "blind insertion" of the endotracheal tube. Only minor movements of the patient's head, neck and jaw are required to insert the intubating laryngeal mask airway device, and once the device has been located in the patient, the endotracheal tube may be inserted with virtually no additional movements of the patient. This stands in contrast to the relatively large motions of the patient's head, neck and jaw that would be required if the endotracheal tube were inserted without the assistance of the intubating laryngeal mask airway device. Furthermore, these devices permit single-handed insertion from any user position without moving the head and neck of the patient from a neutral position, and can also be put in place without inserting fingers in the patient's mouth. Finally, it is believed that they are unique in being devices which are airway devices in their own right, enabling ventilatory control and patient oxygenation to be continuous during intubation attempts, thereby lessening the likelihood of desaturation.

Artificial airway devices of the character indicated, are exemplified by the disclosures of U.S. Pat. No. 4,509,514; U.S. Pat. No. 5,249,571; U.S. Pat. No. 5,282,464; U.S. Pat. No. 5,297,547; U.S. Pat. No. 5,303,697; and by the disclosure of the UK Patent 2,205,499. Such devices with additional provision for gastric-discharge drainage are exemplified by U.S. Pat. No. 4,995,388 (FIGS. 7 to 10); U.S. Pat. No. 5,241,956; and U.S. Pat. No. 5,355,879.

In general, laryngeal mask airway devices aim to provide an airway tube of such cross-section as to assure more than ample ventilation of the lungs, and the designs with provision for gastric drainage have been characterized by relatively complex internal connections and cross-sections calculated to serve in difficult situations where substantial solids could be present in a gastric discharge. As a result, the provision of a gastric discharge opening at the distal end of the mask applicable for direct service of the hypopharynx has resulted in a tendency for such masks to become bulky and unduly stiff, thus making for difficulty in properly inserting the mask. Moreover, undue bulk and stiffness run contrary to the requirement for distal flexibility for tracking the posterior curvature of the patient's throat on insertion, in such manner as to reliably avoid traumatic encounter with the epiglottis and other natural structures of the pharynx.

A number of problems have been experienced with all of these prior types of device. For example, some prior devices seek to prevent occlusion of the airway outlet by parts of the patient's anatomy, such as the epiglottis, by the provision of bars and the like across the outlet. Although such devices function well in most cases, they can make manufacturing more complex, and can affect the performance of devices in use. This is especially so in devices formed from relatively rigid materials, like PVC, as opposed to the more traditional Liquid Silicon Rubber (LSR).

In general, devices formed from materials such as PVC are attractive because they are cheaper to make, and can be offered economically as "single-use" devices. However, there are material differences in PVC and PVC adhesives, such as increased durometer hardness as compared to LSR, which affect how the devices perform in use. For example, it has been observed that for a given volume of air, an LSR cuff will expand to a larger size than a comparable PVC cuff. This superior elasticity allows the LSR cuff to provide an anatomically superior seal with reduced mucosal pressure. To close the performance gap, the PVC cuff must be of reduced wall thickness. However, a PVC cuff of reduced wall thickness, deflated and prepared for insertion, will suffer from poor flexural response as the transfer of insertion force through the airway tube to cuff distal tip cannot be adequately absorbed. The cuff assembly must deflate to a thickness that preserves flexural performance i.e. resists epiglottic downfolding, but inflate so that a cuff wall thickness of less than or equal to 0.4 mm creates a satisfactory seal. And where mask backplates are formed from PVC, as well as cuffs, the fact that the increased durometer hardness of PVC is inversely proportional to flexural performance (hysterisis) means that the flexural performance of the device in terms of reaction, response and recovery on deformation is inferior to a comparable LSR device.

The above described problems are particularly acute in devices which incorporate an oesophageal drain. As mentioned above, in any such device regardless of the material from which it is formed, adding an oesophageal drain in itself adds greatly to complexity of manufacture and can also affect the performance of devices, in terms of ease of insertion, seal formation and prevention of insufflation. These problems can be exacerbated still further if PVC or similarly performing materials are used. For example, the skilled worker will appreciate that in terms of manufacture, the need to provide a drain tube which is sealed from the airway, and which must pass through the inflatable cuff poses a particularly difficult problem. In terms of effects on functionality, the provision of a drain tube can cause unacceptable stiffening of the mask tip area and occlusion/restriction of the airway passage.

BRIEF SUMMARY OF THE INVENTION

According to the invention there is provided a laryngeal mask airway device for insertion into a patient to provide an airway passage to the patient's glottic opening, the device comprising an airway tube, a mask attached to the airway tube, the mask comprising a body having a distal end and a proximal end, a peripheral inflatable cuff, and defining an outlet for gas, the mask being connected to the airway tube for gaseous communication between the tube and the mask, the device further comprising an oesophageal drain, the drain comprising a conduit extending from an inlet at the distal end to an outlet disposed to be outside of the patient when the device is in place in the patient, the conduit including a mask section and an airway tube section, wherein the conduit mask section is formed integrally in the material of the body. Thus it can be seen that the invention addresses the problems which result from the need to incorporate an oesophageal drain, in terms of the performance of the device and also its manufacture.

It is preferred that the conduit extends substantially centrally from the distal end to the proximal end of the mask body, so that a straight and short flow path for liquids and solids is provided.

The mask body may comprise a plate, the plate having a dorsal side and a ventral side, the dorsal side being substantially smooth and having a convex curvature across its width, the conduit being formed on and extending from the ventral side of the plate. This maintains a smooth dorsal profile which aids insertion and patient comfort and keeps the device's dorsal to ventral dimension to a minimum, which further aids insertion.

In a preferred embodiment, the conduit includes an extension part which extends past the distal extent of the mask body. The extension part may be enclosed by, and open out of an integrally formed pocket, and the pocket preferably extends from the material of the inlet. The pocket is preferably inflatable, and most preferably is inflated by gas from the cuff. The pocket and cuff can be sealed together, there being an access way for gas from the cuff to the pocket, and the access way can conveniently be provided by a pinch-off of the cuff.

The extension part may include means to prevent it collapsing under increased air pressure in the pocket. The prevention means may comprise one or more support web formed integrally with the extension part, and the or each support web may extend from the extension part, substantially perpendicular thereto.

The mask preferably comprises a plastics material, such as a shore 50A material, and the airway tube preferably comprises a shore 90A material.

BRIEF DESCRIPTION OF THE DRAWINGS

The invention will further be described by way of example and with reference to the following drawings, in which.

FIG. 8 is a dorsal view of the device of FIG. 4a;

FIG. 10 is a side view, enlarged, of the device of FIG. 4a;

DETAILED DESCRIPTION OF THE INVENTION

Figure 1:
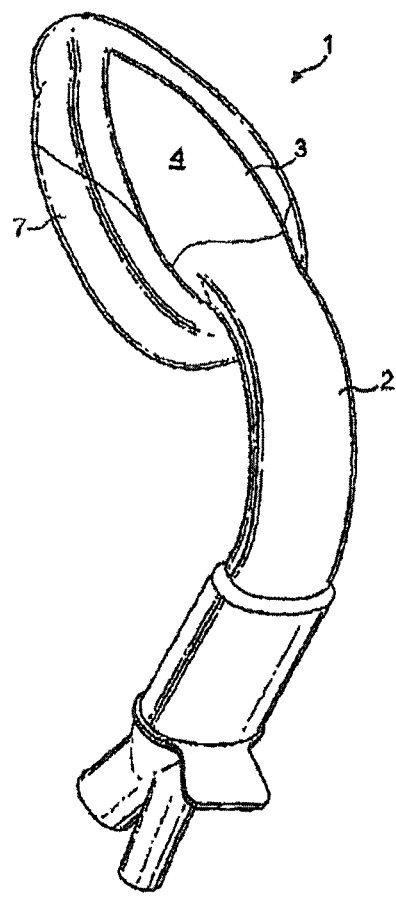
FIG. 1 is a dorsal three quarter perspective view of a device according to the invention.
Figure 2:
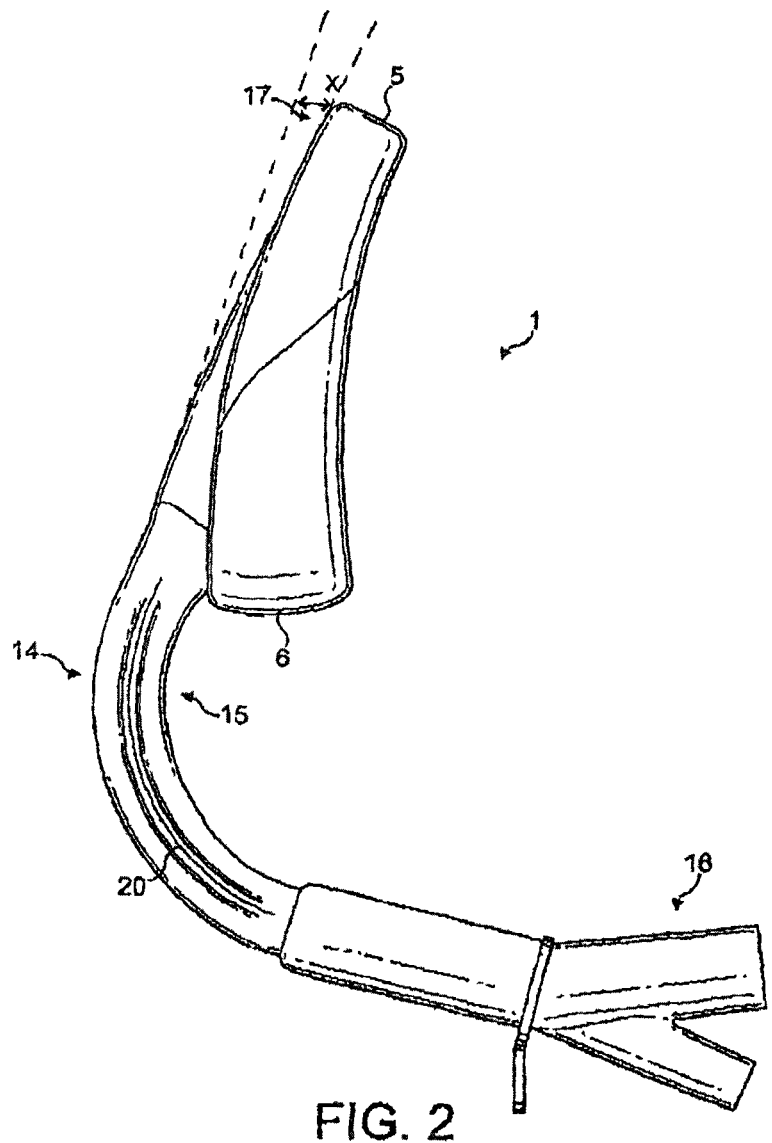
FIG. 2 is a right side view of the device of FIG. 1.
Figure 3:
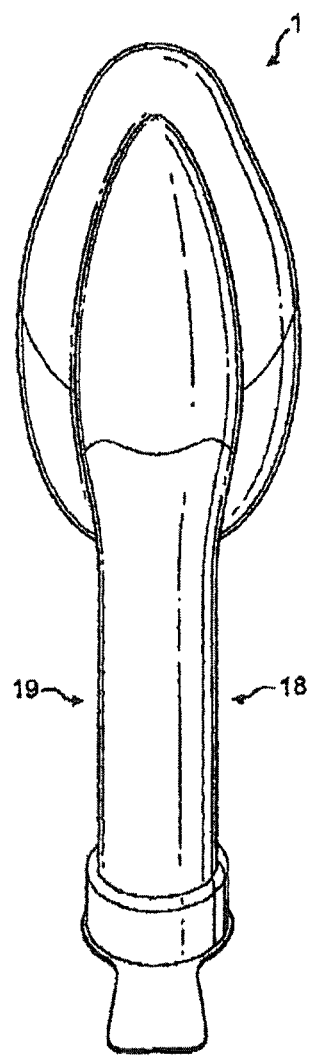
FIG. 3 is a dorsal view of the device of FIG. 1.

Referring now to the drawings, there is illustrated a laryngeal mask airway device 1 for insertion into a patient to provide an airway passage to the patient's glottic opening, the device 1 comprising an airway tube 2 a mask 3 attached to the airway tube 2, the mask 3 comprising a body 4 having a distal end 5 and a proximal end 6, a peripheral inflatable cuff 7, and defining an outlet 8 for gas, the mask 3 being attached to the airway tube 2 for gaseous communication between the tube 2 and the outlet 8, the device 1 further comprising an oesophageal drain 10, the drain 10 comprising a conduit extending from an inlet 12 at the distal end 5 to an outlet 13 disposed to the outside of the patient when the device 1 is in place, the conduit including a mask section 11 and an airway tube section 41, wherein the conduit mask section 11 is formed integrally in the material of the body 4.

As can be seen from the drawings, the device 1, in terms of overall appearance is somewhat similar to prior art devices, in that it consists of the basic parts which make up most if not all laryngeal mask airway devices, i.e. an airway tube 2 and mask 3 which includes a body part 4, and a cuff 7.

For the purposes of description it is appropriate to assign reference names to areas of the device 1 and accordingly with reference to FIGS. 2 to 6, the device 1 has a dorsal side 14, a ventral side 15, a proximal end 16 (in a sense that this is the end nearest the user rather than the patient) a distal end 17 and right and left sides 18 and 19.

Referring firstly to the airway tube 2, in the illustrated embodiments the tube comprises a relatively rigid PVC material such as a shore 90A Colorite PVC moulded into an appropriately anatomically curved shape. The tube 2 has some flexibility such that if it is bent it will return to its original shape. Although it is resiliently deformable in this way, it is sufficiently rigid to enable it to assist in insertion of the device 1 into a patient, acting as a handle and guide. In this embodiment the airway tube 2 does not have a circular cross-section as in many prior devices, but instead is compressed in the dorsal/ventral direction which assists in correct insertion of the device 1, helps prevent kinking, and assists in comfortable positioning for the patient as the shape generally mimics the shape of the natural airway. In this embodiment each side 18, 19 of the airway tube 2 includes a groove or channel 20 extending for most of the tube's length from the proximal to distal ends. These grooves 20 further assist in preventing crushing or kinking of the airway tube 2. Internally the grooves 20 form ridges along the inner surfaces of the sides 18 and 19.

Figure 13:
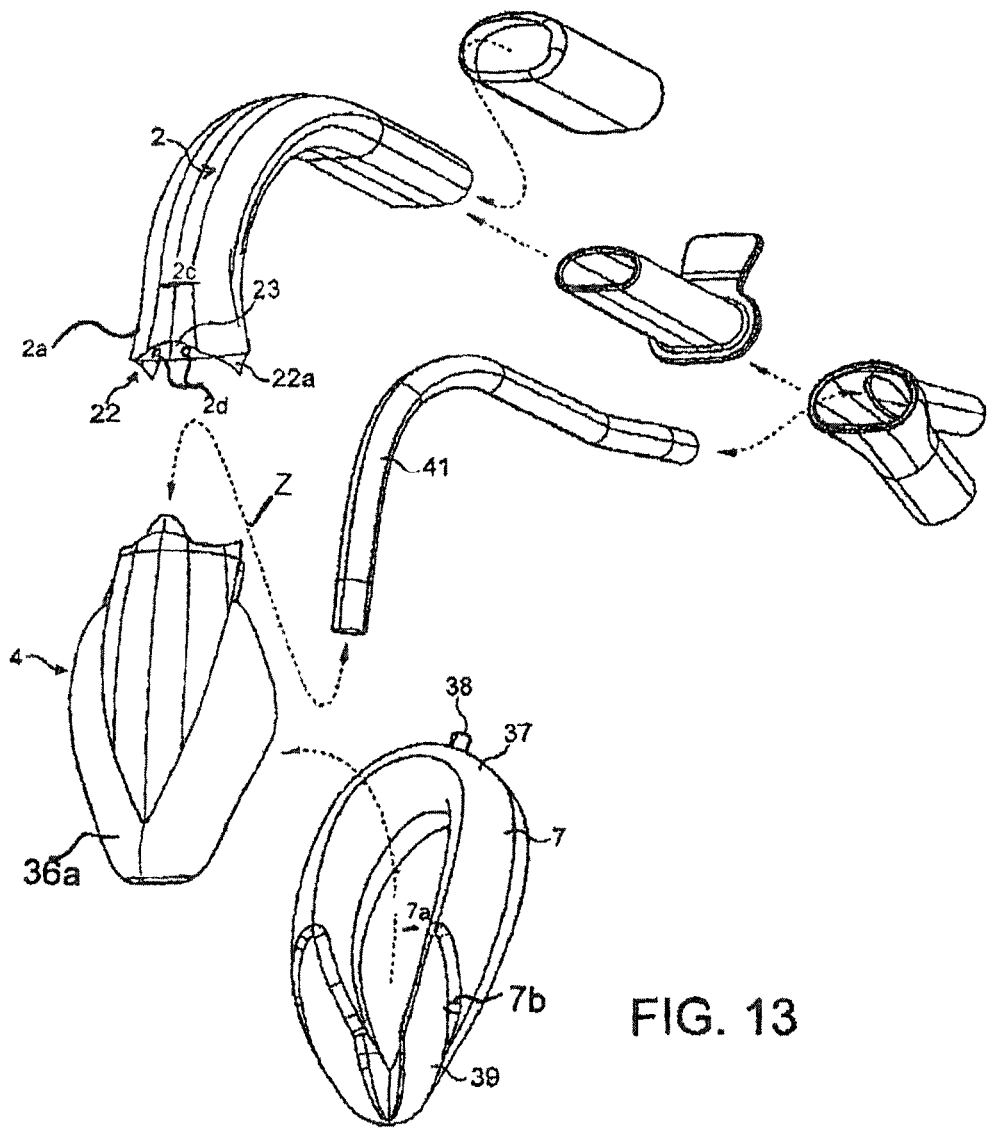
FIG. 13 is an exploded ventral perspective view of a device according to the invention.
Figure 14:
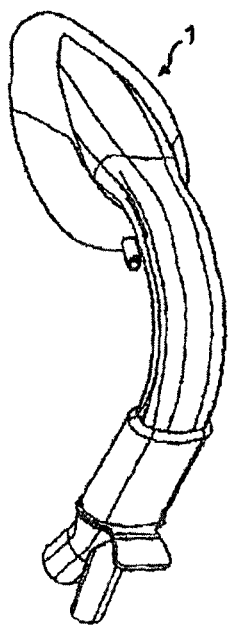
FIG. 14 is a dorsal three quarter perspective view of a device according to the invention.
Figure 15:
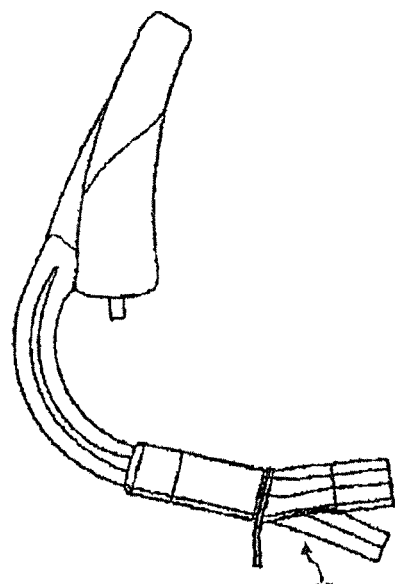
FIG. 15 is a right side view of the device of FIG. 14.
Figure 16:
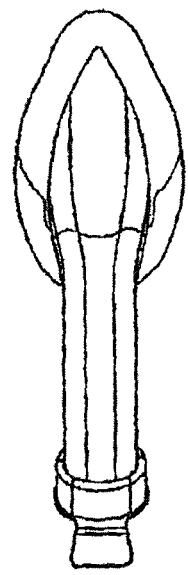
FIG. 16 is a dorsal view of the device of FIG. 14.
Figure 24:
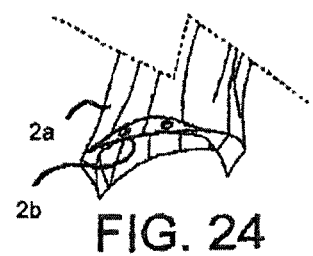
FIG. 24 is a distal end view of a part of the device of FIG. 14.

Referring now to FIG. 13, which shows an exploded view of the device 1, it can be seen that the airway tube 2 includes a flared distal end 22 with surfaces 22*a* disposed to allow for attachment of the tube 2 to the mask 3, conveniently by over moulding of the mask 3 onto the airway tube 2. Thus, the airway tube 2 itself can form a pre-mould used in formation of the device 1, which substantially simplifies manufacturing. Of particular note is the airway tube's dorsal mould surface 23 (FIG. 13). This surface 23 is located at the flared distal end 22, and takes the form of a flat land extending between the outer dorsal surface 2*a* and the inner dorsal surface 2*b* (FIG. 24) of the dorsal wall 2*c*. It includes optional through holes 2*d* to allow the over moulded back plate 4 to lock onto the tube 2, as will be described later on. This feature helps ensure a secure connection between the different materials making up the airway tube 2 and mask 3.

A further feature of the airway 2 is the oesophageal drain tube 41. This drain tube 41 is located within airway tube 2, extending centrally through it from one end to the other, and in this embodiment it is disposed in contact with the inner surface 2*a* of the dorsal wall 2*b* of the airway tube 2, and bounded on each side by raised, smooth walls (not shown) which form a shallow channel through which it runs.

Figure 9:
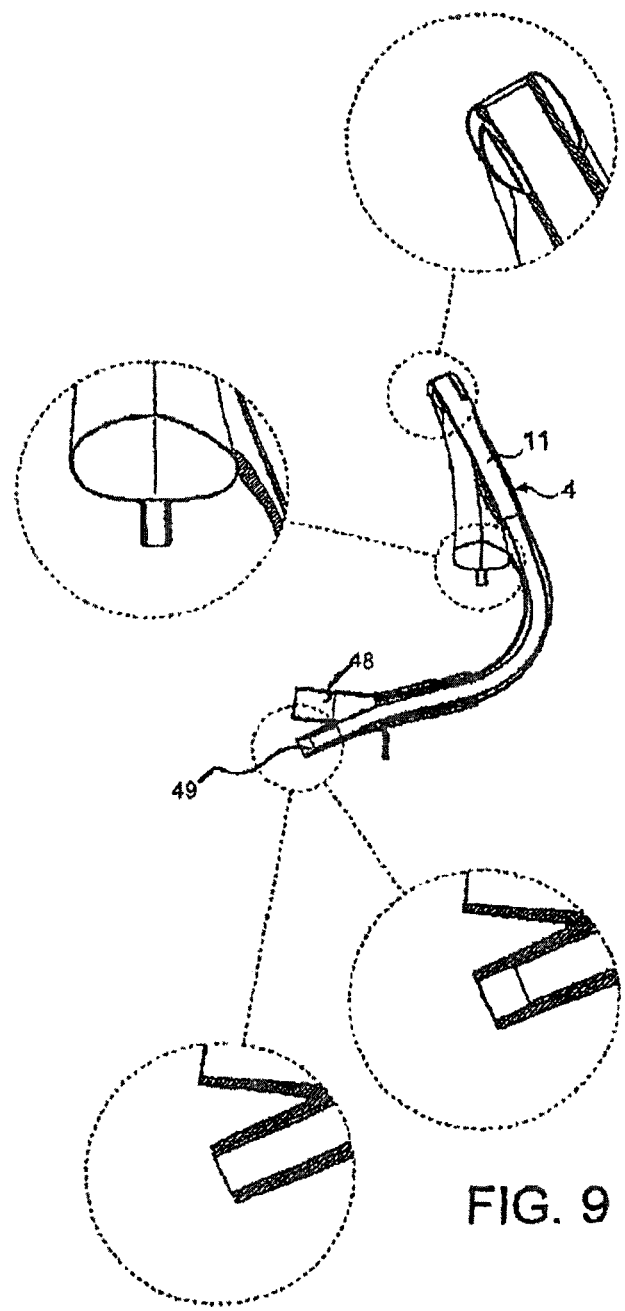
FIG. 9 is a longitudinal sectional view along line Y-Y in FIG. 8.
Figure 10:
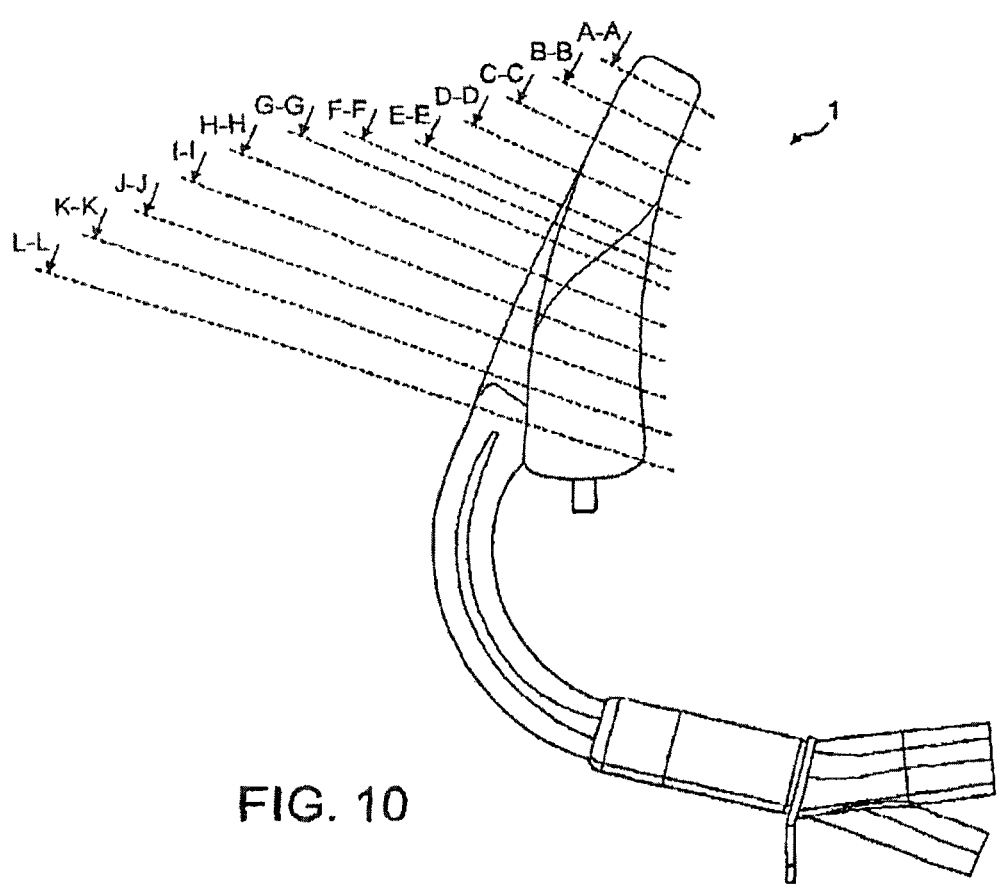
Figure 12:
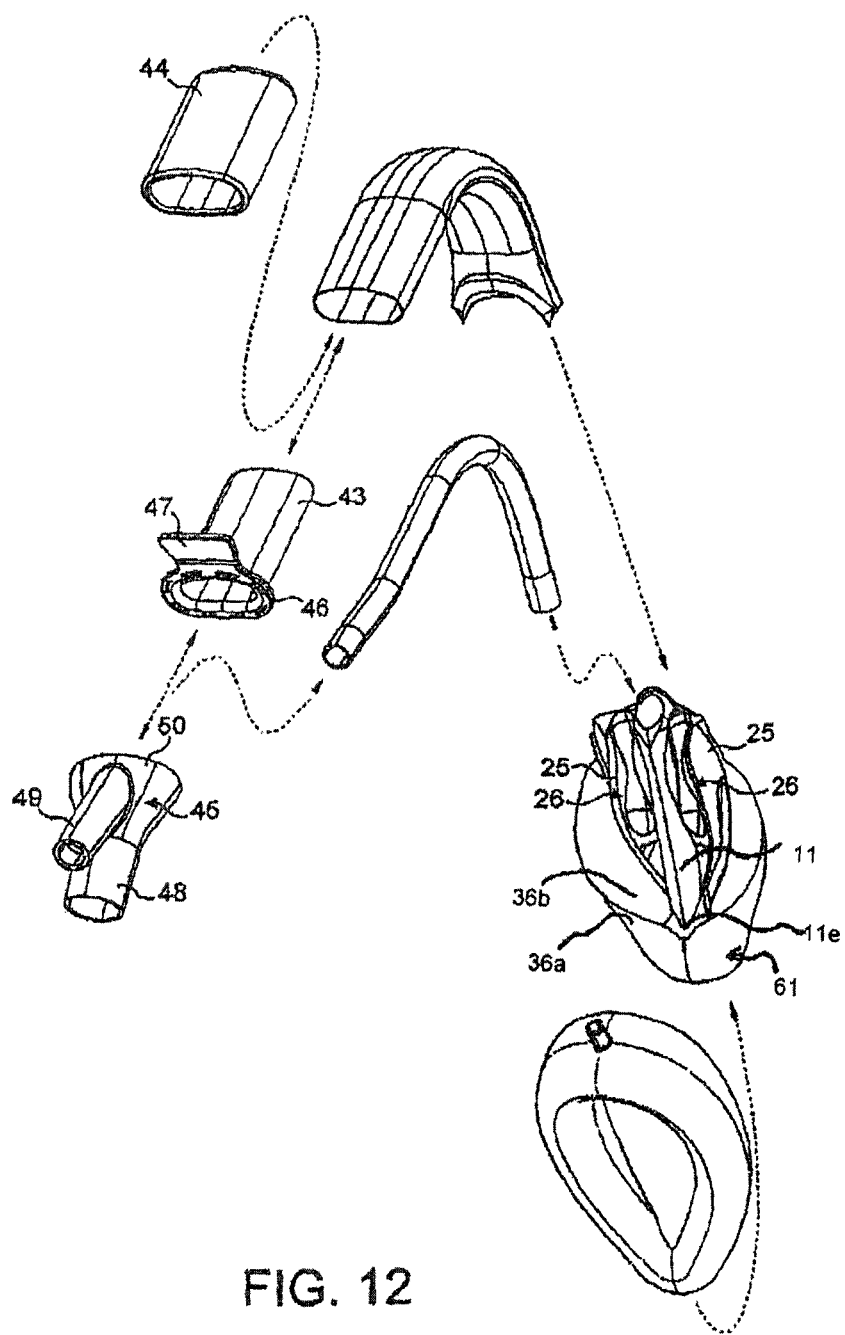
FIG. 12 is an exploded dorsal perspective view of a device according to the invention.

The proximal end of the airway tube 2 is provided with a connector 42, for connection of the device 1 to a gas supply and drain (not shown) as shown for example in FIGS. 12 and 13 and in section in FIG. 9. The connector 42 comprises a connector body 43, an optional bite block 44 and a connector plug 45. The connector body 43 and bite block 44 correspond in shape and dimension with the internal shape of the proximal end of the airway tube 2 such that they fit inside it. The connector body 43 has a perpendicularly extending peripheral flange 46 which extends at one point on its circumference into a tab 47. Connector plug 45 attaches to connector body 43 by adhesive or other suitable means applied to flange 46. The connector plug 45 comprises major and minor bores 48, 49 which both lead into a common atrium 50 at the distal end of the connector plug 45 where it attaches to the connector body 43. Drain tube 41 extends into and through minor bore 49, such that the bore of the airway tube 2 and the bore of the drain tube 41 are separated from one another.

Turning now to the mask 3, the mask 3 consists of two parts, a body part 4 often referred to as a back plate, and a peripheral cuff 7.

The back plate 4 is formed in these embodiments by moulding from a shore 50A Vythene PVC+PU. This material is substantially softer and more deformable than the material of airway tube 2.

Figure 17:
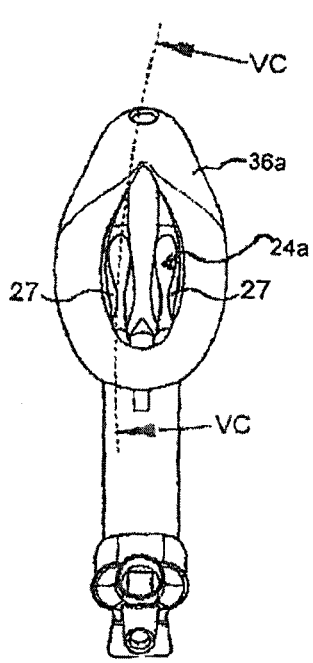
FIG. 17 is a ventral view of the device of FIG. 14.
Figure 23:
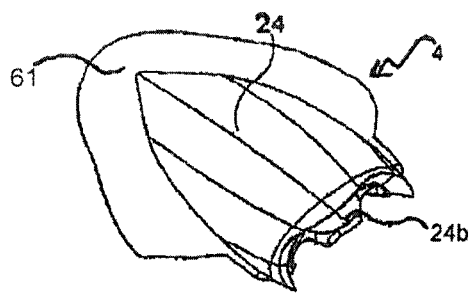
FIG. 23 is a proximal end view of a part of the device of FIG. 14.

Referring now to FIG. 23, the back plate 4 comprises a generally oval moulding when viewed from the dorsal or ventral directions, having a smooth dorsal surface 24, a formed ventral surface 24*a* (FIG. 17), a proximal joining portion 24*b*, and a distal tip 61.

The dorsal surface 24 has a convex curvature from one side to the other, corresponding to the curvature of the dorsal surface of the airway tube 2, and longitudinally, the dorsal surface 24 is also curved, having a curvature beginning at the joining portion 24*b* and extending with constant rate of curvature toward the distal tip 61. As a result the tip 61 is ventrally biased relative to the distal end of the airway tube, in the assembled device 1, the extent of displacement of the distal tip 61 being approximately 20 mm or 10 degrees, in order to produce a curvature in the mask that is suited to the anatomy of the patient. This is shown schematically at X in FIG. 2. On insertion, this displacement of the tip 61 assists the mask in "turning the corner" in the insertion path.

Figure 7:
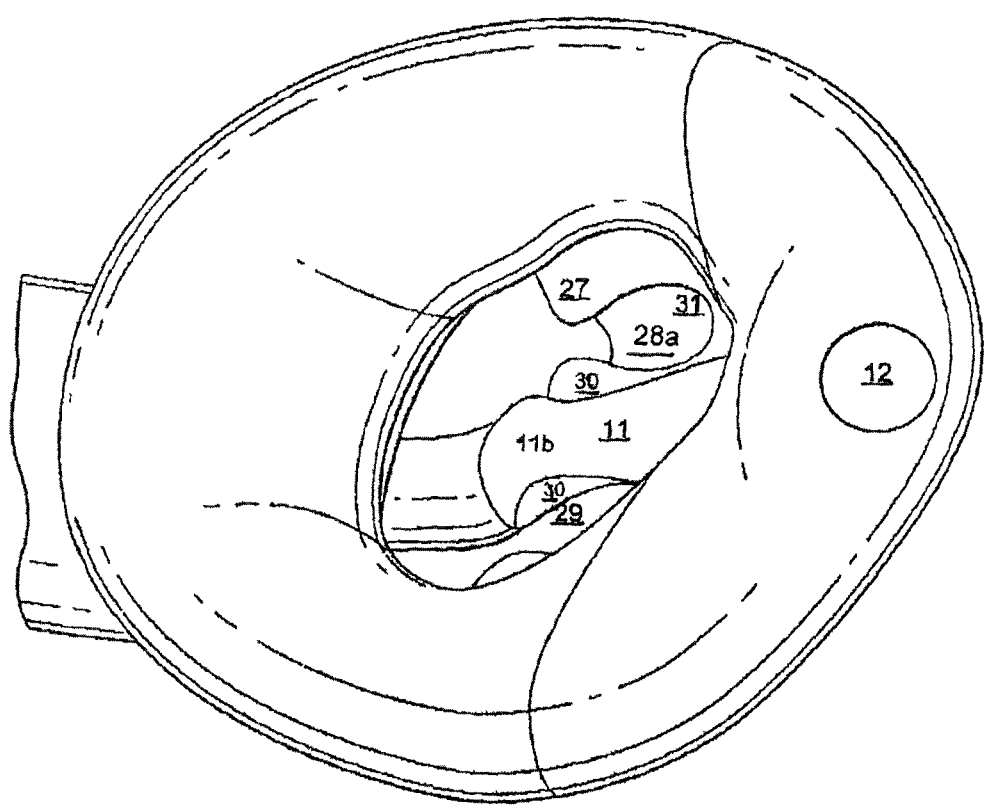
FIG. 7 is an enlarged view of the mask of the device of FIG. 1.
Figure 8:
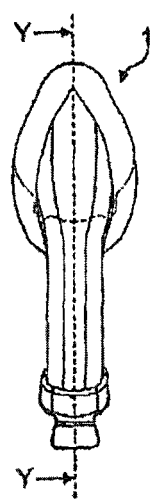
Figure 11A:
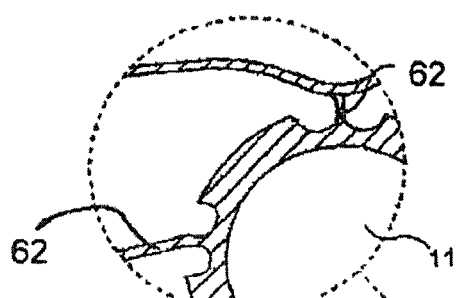
FIGS. 11A to 11K are transverse sectional views along lines A-A to K-K in FIG. 10.
Figure 11A:
Figure 11B:
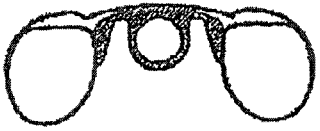
Figure 11C:
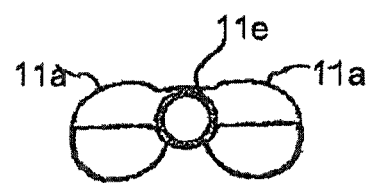
Figure 11D:
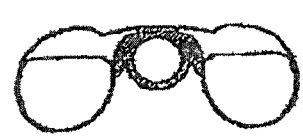
Figure 11E:
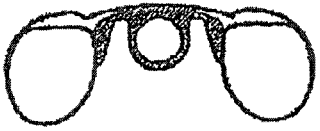
Figure 11F:
Figure 11G:
Figure 11H:
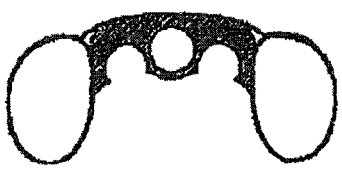
Figure 11I:
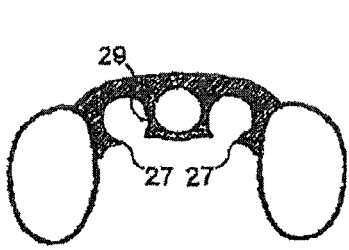
Figure 11J:
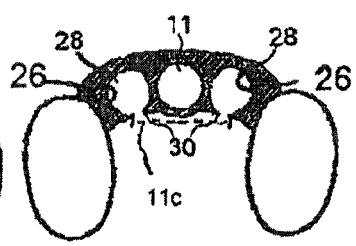
Figure 11K:
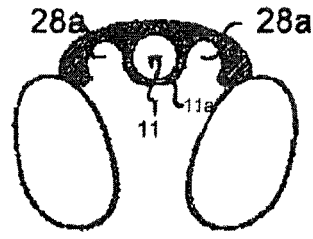

When viewed from the ventral side, the integrally moulded structures of the back plate 4 can best be seen (FIGS. 4,7,12, 17). The precise shape of the ventral side 24*a* of the back plate is illustrated particularly in the sectional views shown in FIGS. 11A to 11K and in the enlarged perspective view in FIG. 7. Referring to the exploded view shown in FIG. 12, the convex curvature of the dorsal surface 24 of the back plate 4 is mirrored in a corresponding concave-curvature on the ventral side. Thus, the ventral surface 24*a* forms a shallow, elongate channel tapering towards the distal tip 61. The channel is bounded by walls 26. The walls 26 have correspondingly shaped, longitudinally extending convex outer surfaces 25. Each wall 26 extends longitudinally substantially the entire length of the back plate 4 from the proximal joining portion 24b towards the distal tip 61. Each wall 26 also has a convex inner surface 28, but rather than terminating at an angle normal to the channel floor, the curve of each wall 26 is continued, the walls curving back over the channel and terminating in inwardly extending webs 27 (FIGS. 7 and 11I and 11J). The inner surfaces 28 of the side walls 26 curve down to form the floor of the channel but do not meet, because the base or floor of the channel is bisected by a longitudinally extending, integrally moulded conduit which is an oesophageal drain tube 11 extending along it for its entire length from joining portion 24b to distal tip 61. Thus, it can be seen that the channel has three longitudinally extending conduits on its inner surface, the two open outer conduits 28a which are minor gas conduits in the assembled device 1, and the central drain tube 11, which forms a septum there between.

Referring now in greater detail to the drain tube 11, it will be seen that the tube 11 has a sufficient diameter such that its upper wall section 11a, i.e. the wall section furthest from the floor of the channel, is on a similar level with the inwardly extending webs 27 of the side walls 26. Furthermore, the upper wall section 11a itself also has outwardly extending webs 30, which taper toward, but do not meet, the correspondingly tapered edges of the webs 27. Thus, the upper surface 11b of the upper wall section 11a of the drain tube 11, and the webs 27, 30, together define a surface 11c shown schematically by a dotted line in FIG. 11J), below the level of which run all three conduits 11, 28a.

Figure 4:
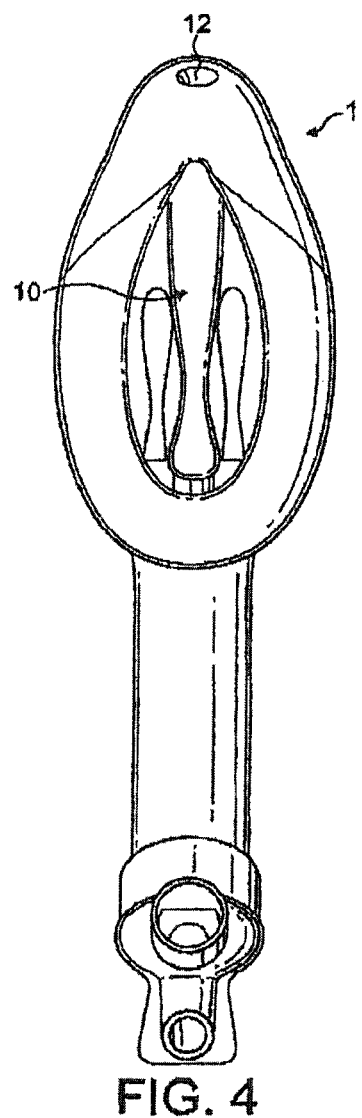
FIG. 4 is a ventral view of the device of FIG. 1.
Figure 4A:
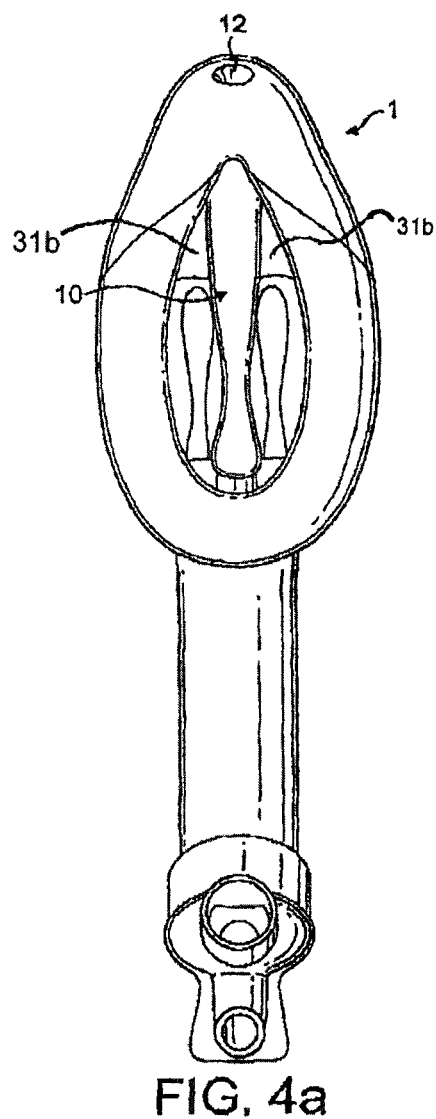
FIG. 4a is a ventral view of a further embodiment of device according to the invention.
Figure 5:
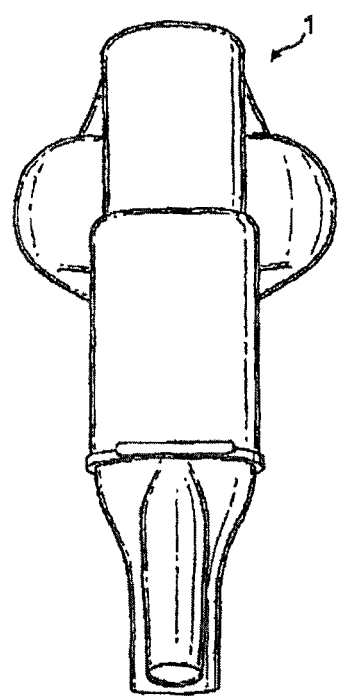
FIG. 5 is an end view, looking from the proximal towards the distal end of the device of FIG. 1.
Figure 6:
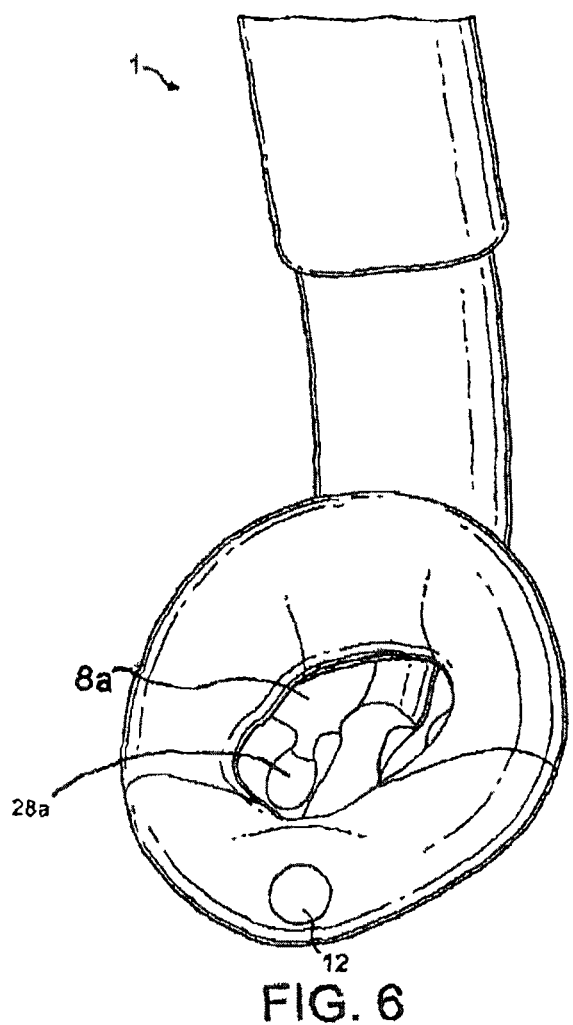
FIG. 6 is an end view, looking from the distal towards the proximal end of the mask of the device of FIG. 1.

Referring now particularly to FIG. 7, it can be seen that although the drain tube 11 extends the full length of the back plate 4 from its proximal joining portion 24b to distal tip 61, the conduits 28a do not extend the full length of the back plate 4, but instead terminate about half way along its length. The floors 31 of the conduits 28a curve gently upwards as they extend towards the distal tip 61 of the back plate 4 until they terminate at a level approximately equal to the level of the webs 27 and 30. In the embodiment shown in FIG. 4a, these areas are hollowed out to form depressions 31b.

Figure 22:
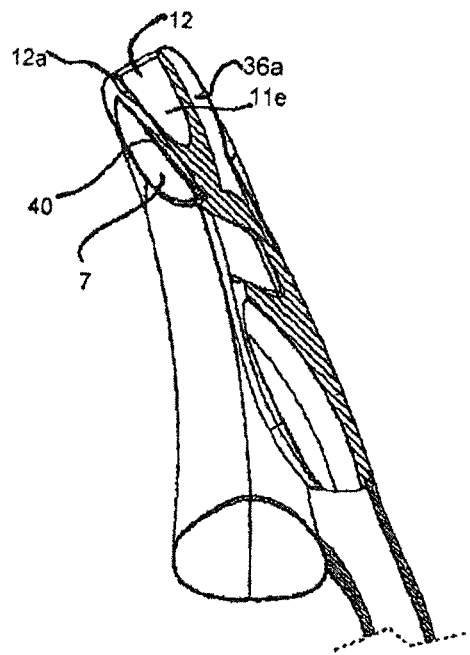
FIG. 22 is a view of section VC-VC in FIG. 17.
Figure 18:
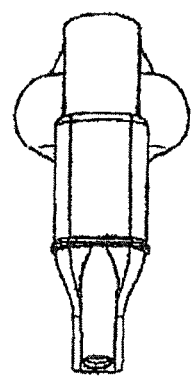
FIG. 18 is an end view, looking from the proximal towards the distal end of the mask of the device of FIG. 14.
Figure 19:
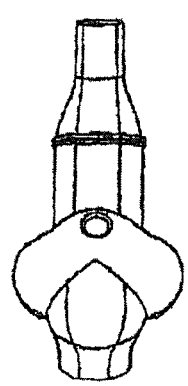
FIG. 19 is an end view, looking from the distal towards the proximal end of the mask of the device of FIG. 14.
Figure 20:
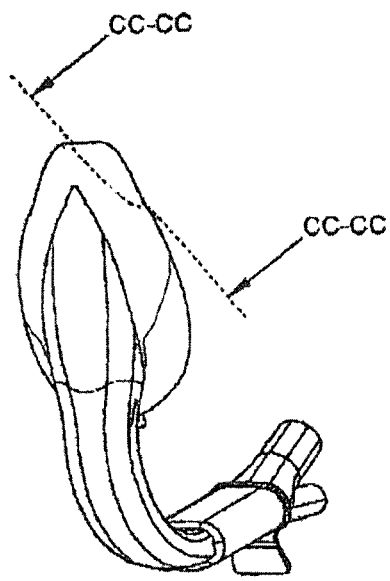
FIG. 20 is a dorsal three quarter perspective view of the device of FIG. 14.
Figure 21:
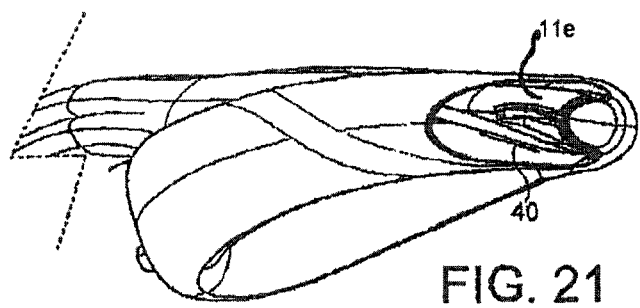
FIG. 21 is a view of section CC-CC in FIG. 20.

As illustrated in FIG. 12 and FIGS. 21 to 23, drain tube 11 extends to distal tip 61, terminating in an opening 12. Thus, an end section 11e of the drain tube 11 protrudes past the end of back plate 4. This end section 11e is provided with dorsal webbing 11a which extends to either side of it, and around it to form a hood or pocket 36a which encloses the end section 11e around its circumference. The hood or pocket 36a is attached to the distal end of the drain tube 11 around the circumference 12a of opening 12 (FIG. 22). This hood or pocket 36a is integrally formed in the material of the back plate 4 at distal tip 61. It completely surrounds and extends from the circumference of the drain tube opening 12 and the joint therebetween is smooth. As illustrated, the ventral extent of the hood is more limited than the dorsal extent, the dorsal extent being to about midway back towards the proximal end of the back plate 4. Referring to sectional views A-A and B-B in FIGS. 11A and 11B, it can be seen that the drain tube 11 is supported on its right and left sides, and on its dorsal surface, by perpendicularly extending webs 62. These webs 62 are integrally formed, and extend back from the opening 12 to the point where the end section 11e meets the extent of the back plate 4. In the illustrated embodiment the dorsal webs 62 extend substantially perpendicularly from the drain tube, but in a preferred embodiment, they may extend to one side or the other, at an angle of less than 90 degrees.

The second part of the mask 3 is the peripheral cuff 7. The cuff 7 is in this embodiment blow moulded PVC and takes the form of a generally elliptical inflatable ring having a central aperture 7a, a relatively deeper proximal end 37 with an inflation port 38 and a relatively shallower distal end 7b tapering to a "wedge" profile 39. As will be appreciated, particularly from the exploded views shown in FIGS. 12 and 13, the cuff 7 is integrally formed in one piece. The wedge profile is provided such that the ratio of dorsal to ventral side surface areas favours the dorsal side. Thus, when deflated the distal end 7b of the cuff 7 will curl with bias from dorsal to ventral side.

In the assembled device 1, drain tube 41 is inserted into airway tube 2, such that it protrudes from proximal end 16. The connector 42 is attached to the airway tube 2 by inserting the connector body 43 and bite block 44 into proximal end 16. The parts are an interference fit and can be secured by adhesive. Plug 45 is attached to connector body 43 via flange 46, such that drain tube 41 passes into minor bore 49, terminating at or adjacent its mouth. Thus it will be seen that the minor bore 49 is solely in fluid communication with drain tube 41, and the major bore 48 is solely in fluid communication with the interior of airway tube 2.

Airway tube 2 is attached to the back plate 4 conveniently by overmoulding the back plate 4 onto the already formed tube 2. Thus, the joining portion 24b of the back plate 4 is moulded onto the dorsal arc of the airway tube 2 (FIG. 13). Secure attachment is facilitated by the surfaces 22a, 23 which provide an increased surface area onto which the moulding occurs, and through-holes 2d, into which back plate material can flow. Drain tube 41 is connected in fluid tight manner to integrally moulded drain 11, as demonstrated by arrow Z (FIG. 13).

The cuff 7 is bonded to the back plate 4 as illustrated in FIGS. 12 and 13 by inserting the wedge shaped distal end 7b of the cuff 7 into the hood or pocket 36a at the distal tip 61 of the back plate 4 such that the wedge surface 39 mates with the inner surface 36b of the hood 36a, and sections of the inner periphery of the cuff 7 mate with convex outer surfaces 25 of back plate walls 26. The cuff 7 is bonded into the hood such that the space between the hood and the cuff is airtight and in this embodiment the cuff is provided with a "pinch off" 40 (FIGS. 21 and 22) putting the cuff 7 and hood 36a into fluid communication so that the air space in the hood can also be inflated, in addition to the cuff 7 itself. However the cuff 7 pinch off does not extend the entire distance towards the distal tip of the cuff to prevent the pressure of inflation occluding the opening 12. The proximal dorsal surface of the cuff is bonded to the ventral arc of the distal end 22 of the airway tube 2. Thus, it will be appreciated that unlike in previous devices incorporating oesophageal drains, in the invention the drain 11 does not pierce the cuff 7, making manufacturing simpler. Furthermore, in prior devices in which the drain pierces the cuff, the cuff must be securely attached around the circumference of the drain tube at the distal tip. Such a secure attachment, for example with adhesive, can make the tip hard, and prevent the drain tube collapsing in the deflated, flattened device, which is highly desirable to enable the mask to pass easily around the curvature of the anatomy. In addition, the acute curvature of a drain tube to cuff joint would be highly susceptible to cracking. In the invention, these problems are avoided because the drain tube 11 is integrally moulded with the hood 36a, which in effect forms a second or minor cuff at the distal tip.

As will be appreciated, the airway of the device 1, which is the conduit through which gas is passed to the patient, is provided by the bore of airway tube 2, which terminates at flared distal end 22. Flared distal end 22 defines, along with back plate 4 and cuff 7, outlet 8 for gas passing from tube 2 into mask 3. Outlet 8 includes three routes by which gas may pass into the mask, namely a main gas conduit 8*a* (FIG. 6), and two minor gas conduits 28*a*.

In use, the deflated device 1 is inserted into a patient in the usual manner with devices of this type. As noted above, the relative rigidity of the airway tube 2 allows a user to grip it and use it to guide the device 1 into the patient, whilst the relatively softer, more compliant material of the back plate means that the mask will more readily deform to negotiate the insertion path without causing damage to the anatomy, and will return to its optimum shape to ensure that a good seal is achieved at the furthest extent of insertion. The ventral displacement of the distal tip 61 relative to the join between the back plate 4 and airway tube 2 further enhances ease of insertion, because the distal tip 61 is thereby presented at the optimum angle to negotiate the "bend" in the insertion path. In devices formed from relatively rigid materials such as PVC, as opposed to the often used LSR these features are particularly important in easing insertion and providing for an enhanced seal.

Referring now to the features of the moulded back plate 4, it will be seen that by providing drain tube 11 integrally moulded in the material of the back plate 4, problems of mask stiffness and difficulty of manufacture in prior designs caused by the presence of a separate drain tube bonded in place with adhesive can be mitigated.

Moreover, with the back plate 4 of the invention, the combination of the centrally located drain tube 11 and minor gas conduits 28*a* assist in solving the problem of occlusion of the airway by parts of the patient's anatomy. The minor gas conduits 28*a* can be thought of as "nostrils" through which gas may continue to pass into the patient even if the main outlet 8*a* becomes occluded by, for example the patient's epiglottis, as the epiglottis will rest upon the septum provided by the drain tube 11. As illustrated particularly in FIGS. 11I and 11J the webs 27, 30 form a partial closure over the conduits 28*a*, to assist in preventing structures such as the epiglottis from falling into and blocking the conduits 28*a*, and also to make the back plate 4 more resistant to lateral compression. It will be appreciated that in this embodiment, the drain 11 forms a convenient septum between the conduits 28*a*, however, in devices with no oesophageal drain, a solid septum could simply be formed in the material of the back plate by moulding. In addition, a larger number of conduits 28*a* could be provided.

Thus, it can be seen that the above described embodiments address the problems of prior art devices in novel and inventive ways.

The invention claimed is:

1. A laryngeal mask airway device for insertion into a patient to provide an airway passage to the patient's glottic opening, the device comprising: an airway tube, a mask attached to the airway tube, the mask comprising a backplate having a distal end and a proximal end, a peripheral inflatable cuff, and defining an outlet for gas, the mask being connected to the airway tube for gaseous communication between the tube and the mask, the device further comprising an oesophageal drain, the drain comprising a conduit extending from an inlet at the distal end to an outlet disposed to be outside of the patient when the device is in place in the patient, the conduit including a mask section and an airway tube section, wherein the conduit mask section is formed integrally in the material of the backplate, and wherein the conduit includes an extension part which extends past the distal extent of the backplate.

2. A device according to claim 1, wherein the conduit extends substantially centrally from the distal end to the proximal end of the backplate.

3. A device according to claim 1, the backplate having a dorsal side and a ventral side, the dorsal side being substantially smooth and having a convex curvature across its width, the conduit being formed on and extending from the ventral side of the backplate.

4. A device according to claim 1, wherein the extension part is enclosed by, and opens out of an integrally formed pocket.

5. A device according to claim 4, wherein the pocket extends from the inlet.

6. A device according to claim 1, wherein the pocket is inflatable.

7. A device according to claim 6, wherein the pocket is inflated by gas from the cuff.

8. A device according to claim 7, wherein the pocket and cuff are sealed together, there being an access point for gas from the cuff to the pocket.

9. A device according to claim 8, wherein the access way is provided by a pinch-off of the cuff.

10. A device according to claim 1, wherein the extension part includes means to prevent it collapsing under increased air pressure in the pocket.

11. A device according to claim 10, wherein the prevention means comprises one or more support web formed integrally with the extension part.

12. A device according to claim 11, wherein the or each support web extends from the extension part, substantially perpendicular thereto.

13. A device according to claim 11, wherein the airway tube comprises a shore 90A material.

14. A device according to claim 1, wherein the mask comprises a plastics material.

15. A device according to claim 1, wherein the material is a shore 50A material.

* * * * *